United States Patent [19]

Fogel

[11] Patent Number: 6,126,951
[45] Date of Patent: Oct. 3, 2000

[54] EMOLLIENT ESTERS BASED UPON CAPRYL ALCOHOL AND ISOSTEARIC ACID

[75] Inventor: Arnold W. Fogel, Upper Saddle River, N.J.

[73] Assignee: Bernel Chemical Company, Inc., Englewood, N.J.

[21] Appl. No.: 09/115,029

[22] Filed: Jul. 14, 1998

[51] Int. Cl.[7] .............................. A61K 7/00; A61K 9/00; A61K 31/21; A61K 31/23; B01F 17/00
[52] U.S. Cl. ...................... 424/401; 424/400; 514/506; 514/552; 514/873; 514/938; 516/53
[58] Field of Search ................................... 424/400, 401; 514/873, 938, 506, 552; 252/306; 516/53

[56] References Cited

U.S. PATENT DOCUMENTS

| | | |
|---|---|---|
| 3,687,883 | 8/1972 | Korf . |
| 4,074,978 | 2/1978 | Panzer . |
| 4,184,978 | 1/1980 | France et al. . |
| 4,228,151 | 10/1980 | Lang et al. . |
| 4,534,963 | 8/1985 | Gordon . |
| 5,025,004 | 6/1991 | Wu et al. . |
| 5,221,286 | 6/1993 | Singleton . |
| 5,436,006 | 7/1995 | Hirose et al. . |
| 5,451,254 | 9/1995 | Andrean et al. ..................... 106/503 |
| 5,476,648 | 12/1995 | Fogel . |
| 5,525,588 | 6/1996 | Michetti . |
| 5,620,682 | 4/1997 | Fogel . |
| 5,656,664 | 8/1997 | O'Lenick, Jr. . |
| 5,658,575 | 8/1997 | Ribier et al. . |
| 5,660,865 | 8/1997 | Pedersen et al. . |
| 5,674,475 | 10/1997 | Dahms et al. . |
| 5,690,918 | 11/1997 | Jacks et al. . |
| 5,730,893 | 3/1998 | Wyman et al. . |
| 5,785,979 | 7/1998 | Wells . |
| 5,955,062 | 9/1999 | McEleney et al. ................. 424/59 |
| 5,961,961 | 10/1999 | Dobkowski et al. ................ 424/59 |

FOREIGN PATENT DOCUMENTS

| | | |
|---|---|---|
| 08149989 A2 | 6/1996 | Japan . |
| 08149991 A2 | 6/1996 | Japan . |

*Primary Examiner*—Shelley A. Dodson
*Assistant Examiner*—Marina Lamm
*Attorney, Agent, or Firm*—Henry D. Coleman; R. Neil Sudol

[57] ABSTRACT

The present invention relates to a novel emollient compound capryl isostearate, which is obtained from capryl alcohol and isostearic acid. These emollient compounds may then be used in dermatological products for their unexpected characteristics and as silicone-free carbon based replacements for the volatile cyclomethicones.

10 Claims, No Drawings

EMOLLIENT ESTERS BASED UPON CAPRYL ALCOHOL AND ISOSTEARIC ACID

FIELD OF THE INVENTION

The present invention relates to novel synthetic ester compounds which are used advantageously in dermatological products for their unexpected characteristics of light emolliency, and lubricity without oiliness. The invention relates to compounds comprising a new emollient ester product, namely capryl isostearate and the use of this emollient ester in dermatological compositions. In one aspect of the present invention, compounds according to the present invention are advantageously used to substitute for cyclomethicones, i.e., cyclic silicone compounds which are added to a number of dermatological compositions for their solvency, light emolliency (prior to evaporation) and their volatility. It unexpectedly has been discovered that the inclusion of compounds according to the present invention will instill in dermatological compositions the characteristics of light emolliency, lubricity without oiliness and a lightness similar to that of the cyclomethicones or cyclic silicones. The present compounds are advantageously used as substitutes for the cyclomethicones because they provide a similar "initial feel" (as soon as the compound is placed on the skin until about 30 minutes after being placed on the skin) and a superior "lasting feel", with respect to emolliency as well as moisturizing characteristics, without producing the untoward effects associated with the cyclomethicones, and in particular, safety concerns.

BACKGROUND OF THE INVENTION

The present inventor has worked for the past forty years, both as a formulator of finished products and creator of individual raw materials, to instill emolliency and to provide emollient compounds and other additives for use in dermatological products. Starting in 1957, the inventor, as a formulating chemist of dermatological products, has been involved in using esters for their surface active and emollient properties which they contribute to a finished formulation. Some typical esters, many of which are still used by the inventor today, include the following:

1. Di isopropyl adipate;
2. Isopropyl linoleate;
3. Decyl/isodecyl oleate;
4. Glyceryl monostearate;
5. Cetyl/myristyl lactate;
6. Glyceryl dilaurate;
7. Glycol stearate;
8. PEG 400 Monostearate (other PEG fatty esters);
9. Isostearyl neopentanoate;
10. Isocetyl stearate;
11. Isocetyl stearoylstearate;
12. Myristyl myristate;
13. Octyl palmitate;
14. Isopropyl palmitate;
15. Isopropyl Myristate;
16. Isopropyl lanolate;
17. Glyceryl tricaprylate/caprate;
18. Propylene glycol tricaprylate/caprate;
19. Cetyl palmitate;
20. Vegetable Oils (various liquid and solid);
21. Sorbitan and ethoxylated sorbitan esters;
22. Alkoxylated fatty acid esters;
23. Glucan esters;
24. Stearyl Stearate;
25. Stearyl stearoyl stearate;
26. Dicapryl fumarate;
27. Propylene glycol isoceteth-3-acetate;
28. Dipropylene glycol isoceteth-20-acetate;
29. Octyldodecyl neopentanoate;
30. Di-$C_{12-15}$ Alkyl fumarate;
31. Di-behenyl fumarate;
32. Tri-isocetyl citrate;
33. Tri-Octyldodecyl citrate;
34. Behenoyl Stearic Acid;
35. $C_{12-15}$ Alkyl Octanoate;
36. Propyleneglycol myristyl ether acetate;
37. Neopentylglycol di-octanoate;
38. Neopentylglycol di-isostearate;
39. Tri-capryl citrate;
40. Dicapryl maleate;
41. Hexyl laurate;
42. Lauryl caprylate/caprate;
43. Glycereth cocoate.

Throughout his extensive research with emollients, until the present invention, the inventor has never seen an emollient (excluding the cyclomethicones) feel as "dry" with regard to lubricity and "after feel", and which "disappears as quickly on the skin" as the compound of the present invention.

The cyclomethicones, available from Dow Chemical Corp., among other companies as cyclomethicone 344 and 345, are cyclic tetrameric and pentameric dimethicone compounds which are liquid at room temperature, but which also have a sufficiently low boiling point to be useful as delivery vehicles for dermatological compositions because of their ability to rapidly evaporate from the skin. In the early 1990's, the cyclomethicones very rapidly became a delivery vehicle or emollient of choice for many products including hair care products such as shampoos and conditioners, antiperspirants and deodorants and skin and body lotions. Recently, the use of the cyclomethicones has come under increased scrutiny, as those utilizing the cyclomethicones in dermatological products wrestle with untoward side effects such as significant "problems" with safety studies.

OBJECTS OF THE INVENTION

It is an object of the present invention to provide novel emollient compounds which exhibit characteristics in parity with the cyclomethicones relating to lubricity and "after feel" and which "disappear" from the skin, without exhibiting the untoward safety problems of the cyclomethicones.

It is another object of the invention to provide basic formulations which can be used in formulating dermatological (including cosmetic) compositions to instill the final compositions with the favorable characteristics of the present emollient compounds.

It is still an additional object of the invention to provide "all green" (ie., derived from plant in contrast to animal sources) compounds, compositions and final products.

These and other objects of the present invention may be readily gleaned from the description of the invention which follows.

BRIEF DESCRIPTION OF THE INVENTION

The present invention relates to emollient compounds of the chemical formula:

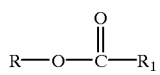

where R is the capryl radical

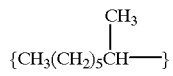

and $R_1$ is derived from isostearic acid (7-methylheptadecanoic acid) or a mixture of isostearic acid and stearic acid (octadecanoic acid) wherein the weight ratio of isostearic acid to stearic acid ranges from approximately 20:1 to 1:1, preferably about 3:2 to 1:1, most preferably about 3:2. In preferred aspects of the present invention, where $R_1$ is derived from isostearic acid or a mixture of isostearic acid and stearic acid comprising at least about 60% by weight of isostearic acid, the emollient compounds have a cloud point of about +8° C. or less (about +2° C. to about+8° C.) and at this temperature, the product is actually sparkling clear. The material also has an ideal freeze/thaw temperature range, e.g., about +15–25 ° C.(i.e., there is no need to separately heat and stir to obtain a homogeneous sparking clear mixture which is very important for quality control and compounding). This unexpected characteristic of the emollient compounds of the present invention makes them ideal for handling and formulating products without requiring significant additional effort.

Compositions according to the present invention comprise the emollient compounds in combination with other additives, depending upon the type of composition desired. In one aspect of the present invention, a dispersible bath oil is contemplated, the bath oil comprising about 75% to about 97.5% by weight of capryl isostearate and about 2.5% to about 25% by weight of a dispersing agent.

In other aspects, compositions according to the present invention comprise the previously disclosed emollient compounds in combination with other components and include oil-in-water emulsions (e.g., lotions) and water-in-oil emulsions (e.g., creams), stick bases, lotion bases and Non-dispersible (floating) bath oil bases.

Quite unexpectedly, the present compounds exhibit parity with the cyclomethicones in terms of lubricity ("dryness", i.e. non-oily) and "after feel" (i.e., the present compounds seem to disappear after a short period of time on the skin) and are superior to the cyclomethicones with respect to lasting emolliency and compatibility with the skin as well as moisturizing characteristics. Thus, the compounds evidence a parity with the cyclomethicones with respect to those features which are desireable, and an advantage compared to the cyclomethicones with respect to those features which are less desirable. Thus, the emollient compounds of the present invention may be used generally as substitutes exhibiting the same or more favorable characteristics for the cyclomethicones in dermatological products.

Capryl isostearate emollient compounds of the present invention exhibit the following favorable characteristics:

1. Favorable color, odor, safety and stability;
2. Favorable freeze/thaw characteristics (easy to handle and compound);
3. Favorable solubility characteristics—the compounds are easy to formulate;
4. Provides desired properties for its structure: dry, non-oily lubricity; lasting emolliency, moisturization and good feel on the skin;
5. Economical (preferably, uses captured chemistry).

DETAILED DESCRIPTION OF THE INVENTION

The following terms shall be used to describe the present invention:

The term "capryl" is used throughout the specification to describe radicals derived from 2-octanol. Capryl is used to describe a fully saturated hydrocarbon radical of eight carbon units and is structurally depicted as $CH_3(CH_2)_5CH(CH_3)$—or

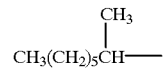

(methylheptyl). The branching of the capryl radical is believed to be at least partially responsible (in combination with the branching of the isostearate portion of the molecule) for the advantageous liquidity of the emollient compounds of the present invention.

The term "isostearic" is used throughout the specification to describe radicals derived from branched-chain $C_{18}$ fatty acids which are reacted with capryl alcohol (2-octanol) to produce capryl isostearate pursuant to the present invention. In its broadest terms, isostearic acid refers to a population of isomerized $C_{18}$ fatty acids, the major component (i.e., at least about 60% by weight of which) is 7-methylheptadecanoic acid. In its narrowest embodiment, isostearic acid refers to pure (i.e. greater than about 95% by weight and more preferably greater than ab out 98% by weight purity) 7-methyiheptadecanoic acid . In a preferred embodiment according to the present invention, isostearic acid refers to a mixture of about 55–65% (most preferably about 60%) by weight isostearic acid, about 30–35% (most preferably about 32%) by weight stearic acid and about 5–10% (most preferably about 8%) by weight palmitic acid. Isostearic acid is prepared from tall oil by dimerization with catalyst, heat and pressure to give isooleic acid which is hydrogenated and further reacted to provide a mixture of about 60% isostearic acid and 40% stearic acid (actually, a mixture of about 80:20 stearic acid/palmitic acid). This mixture may then be further separated to provide essentially pure isostearic acid and stearic acid.

The term "capryl isostearate" refers to emollient compounds/compositions according to the present invention which are derived from capryl alcohol and pure isostearic acid or a mixture of isostearic acid and no more than about 30–50%, preferably no more than about 40% by weight (of the combined weight of isostearic acid and stearic acid) of stearic acid or a mixture of stearic acid and palmitic acid. All of the above derived compounds/compositions are included under the label capryl isostearate. The individual components capryl alcohol and isostearic acid (including versions which contain isostearic acid, stearic acid and palmitic acid in a typical weight ratio of 60:32:8) may be obtained from Union Camp Corp., Jacksonville, Fla., USA.

The term "effective amount" is used throughout the specification, including the claims, to describe amounts or concentrations of individual components used in compositions according to the present invention for the purpose for which they are included in the present compositions. For example, where an emulsifier is used, an "effective amount" of an emulsifier is that amount which is effective for emulsifying the composition described.

The term "emollient base" is used throughout the specification to describe compositions which comprise capryl isostearate. Emollient bases for use in the present invention include stick bases which comprise capryl isostearate and a stiffening or hardening agent, among numerous additional components; lotion bases which comprise capryl isostearate and emulsifier, and bath oil bases which comprise capryl isostearate and a dispersing agent or capryl isostearate and an oil (Non-dispersible bath oil), as described in greater detail herein.

The term "hardening" or "stiffening" agent is used throughout the specification to describe a synthetic or natural wax which is used to produce stick base compositions for use in the present invention. Exemplary synthetic or natural waxes for use in this aspect of the present invention include, for example, di-behenyl fumarate (Marrix® 222, available from Bemel Chemical Co., Englewood, N.J.), camauba wax, beeswax, paraffin wax, ozokerite wax, fatty alcohols such as stearoyl alcohol and stearic monoethanolamide, among others. The preferred stiffening agent for use in the present invention is di-behenyl fumarate.

The term "dispersing agent" is used throughout the specification to describe compounds which are added to capryl isostearate in order to produce certain compositions according to the present invention and in particular, bath oil compositions according to the present invention. A dispersing agent is included in compositions according to the present invention, such as bath oil compositions, in order to disperse the capryl isostearate in water. Preferred dispersing agents for use in the present compositions include, for example, propylene glycol-isoceteth-3-acetate (Hetester® PHA, available from the Bernel Chemical Co. Englewood, N.J.), among numerous others, including PEG 200, 400, 600, mono- or diesters of $C_{12}$–$C_{18}$ fatty acids, ethoxylated $C_{12}$–$C_{22}$ fatty alcohols, among others, including any cosmetically acceptable oil soluble, water dispersible surfactant.

The term "stearic" is used throughout the specification to describe radicals derived from straight-chain $C_{18}$ fatty acids which may constitute a minor component within a mixture of fatty acids otherwise described as isostearic acid herein. Stearic acid is usually found in nature as a triglyceride in animal fats, especially tallow. In the present invention, stearic acid, which is found as a minor component in the isostearic acid mixture, which is preferably prepared from tall oil. In general, in the present invention, stearic acid comprises no more than about 50% by weight of the total weight of fatty acids in the mixture of fatty acids referred to as isostearic acid. In a preferred embodiment according to the present invention, stearic acid comprises about 30–35% (most preferably about 32%) by weight of the isostearic acid used to synthesize capryl isostearate hereunder. Stearic acid also refers herein to mixtures of stearic acid and palmitic acid (straight chain $C_{16}$ fatty acid) as well as other $C_{16}$ fatty acids, wherein the amount of stearic acid in such mixture is at least about 50% by weight, more preferably at least about 80% by weight.

The term "emulsifying agent" or "emulsifier" is used throughout the specification to describe a compound which is added to certain compositions according to the present invention in order to compatibilize water and capryl isostearate, for example, to produce oil-in-water (lotions) and water-in-oil (creams) emulsions according to the present invention. Emulsifiers as used generally are considered surfactants which exhibit good surface activity and produce a low interfacial tension in the system in which it is used. Mixtures of emulsifiers also may be preferred, especially where one of the emulsifiers is preferentially oil-soluble and at least one of the emulsifiers is preferentially water-soluble (or dispersible). One of ordinary skill in the art may readily determine the type and amount of emulsifier or emulsifying system (group of emulsifiers) which may be used in the compositions according to the present invention which include water.

Exemplary emulsifiers for use in the present invention may be non-ionic, anionic, cationic or amphoteric and include, any cosmetically acceptable emulsifier. Emulsifiers for use in the present invention include, for example, linear or branched chain alcoholic ethoxylates and ethoxysulfates, alcohol ethoxylates, sorbitan esters and ethoxylated polysorbate esters, ethoxylated alkylphenols, for example, polyethoxynonylphenols, phenoxypolyalkoxyalcohols, for example, nonylphenoxypoly(ethyleneoxy)ethanol and nonylphenoxypolyethoxyethanol, hydrophobic or hydrophilic compounds such as ethylene oxide condensation products with higher fatty acids, higher fatty alcohols, or alkylated aromatic hydrocarbons, higher molecular weight poly propylene glycols, amide and amine condensation products of which N-bis(2-hydroxyethyl)-lauramide is exemplary. Other nonionic emulsifiers may include polyoxyethylene ethers including polyoxyethylene isohexadecyl ether, such as Arlasolve™ 200 (available from ICI Americas), polyoxyethylene lauryl ether such as Brij 35™, polyoxyethylene stearyl ether, for example Brij $_{72}$™ and Brij 78™ and polyoxypropylenestearyl ether, among others. Other exemplary emulsifiers include ethoxylated lanolin, for example, Lanogel 41 (Amerchol, Inc. Edison, N.J.), alkyl and dialkyl succinate compounds, including combinations of these emulsifiers.

Exemplary anionic emulsifiers for use in the present invention include, for example, soaps, such as triethanolamine stearate, alkaline salts of sulfuric acid esters of polyhydric alcohols, e.g. lauryl sulfate, cetyl sulfate, etc., higher fatty alcohol sulfates, such as those derived from cocoanut oil, hydroxyl sulfonated higher fatty acid esters such as fatty acid esters of 2,3-dihydropropane sulfonic acid, high fatty acid esters of low molecular weight alkylol sulfonic acids, e.g., oleic acid ester of isethionic acid, sulfated higher fatty acid alkylolamides such as ethanol amide sulfates, higher fatty acid amides of amine alkyl sulfonic acids, such as lauric amide of taurine, among others and armomatic containing anionic anionic synthetic emulsifiers. Exemplary amphoteric emulsifiers include, for example, salts of N-alkyl compounds of betaamino propionic acid wherein the alkyl group is derived from a fatty acid such as a mixture of cocoanut oil fatty acids, among others. Exemplary cationic surfactants include ammonium and quaternary salts of fatty amines and substituted fatty amines, among others. All of the above emulsifiers, among numerous others, may be used alone or in combination with other emulsifiers to make compositions according to the present invention. It is noted that when using a cationic emulsifier, caution must be maintained in selecting a thickener for use in the present invention.

Particularly preferred emulsifiers for use in the present invention include propylene glycol-isoceteth-3-acetate (Hetestero PHA, available from Bemel Chemical Co., Englewood, N.J., USA), self-smulsifying glyceryl monostearate cetearyl alcohol, ceteareth-20 and mixtures, thereof.

The term "emollient oil" or "oil" is used throughout the specification to describe any of various lubricious, hydrophobic and combustible substances obtained from animal, vegetable and mineral matter, but preferably are derived from vegetable (i.e., non-animal, "green" sources) which may be included to embellish capryl isostearate in certain compositions or lower the cost of certain compositions according to the present invention. Emollient oils for use in the present invention may include petroleum-based oil derivatives such as purified petrolatum and mineral oil. "Non-polar" oils are generally oils such as petrolatum or mineral oil or its derivatives which are hydrocarbons and are more hydrophobic and lipophilic compared to synthetic oils, such as esters, which may be referred to as "polar" oils. It is understood that within the class of oils, the use of the terms "non-polar" and "polar" are relative within this very hydrophobic and lipophilic class, and all of the oils tend to be much more hydrophobic and lipophilic than the water phase which is used to produce the water-in-oil and oil-in-water emulsions as well as Non-dispersible (floating) bath oils of the present invention. Preferred hydrophobic oils for use in the present invention include mineral oil and petrolatum. Preferred less hydrophobic (i.e., more polar) oils for use in the present invention include a number of maleates, neopentanoates, neopentanoyls, citrates and fumarates, and any other cosmetically acceptable ester emollient. In the case of Non-dispersible (floating) bath oils, preferred emollient oils other than the capryl isostearate include mineral oil and vegetable oil.

Additional oils for use in the present invention may include, for example, mono-, di-and tri- glycerides which may be natural or synthetic (derived from esterification of glycerol and at least one organic acid, saturated or unsaturated, such as for example, butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from seeds or nuts and include drying oils, for example, linseed, iticica and tung, among others; semi-drying oils, for example, soybean, sunflower, safflower and cottonseed oil; non-drying oils, for example castor and coconut oil; and other oils, such as those used in soap, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others, but these are less preferred. In addition, a number of other oils may be used, including $C_{12}$ to $C_{30}$ (or higher) fatty esters (other than the glyceride esters, which are described above) or any other acceptable cosmetic emollient.

The inclusion of mineral oil or vegetable oils as preferred emollient oils in Non-dispersible (floating) oil baths is also contemplated by the present invention.

The present invention relates to novel emollient compounds of the formula:

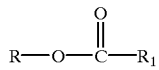

where RO is derived from capryl alcohol and

is derived from isostearic acid (7-methylheptadecanoic acid) or a mixture of isostearic acid and stearic acid (octadecanoic acid) such that the ratio of isostearic acid to stearic acid ranges from approximately 20:1 to 1:1, preferably about 3:2 to 1:1, most preferably is about 3:2 (60:40 ratio of isostearic acid to stearic acid). The emollient compounds of the present invention exhibit unexpected characteristics such as favorable, dry, non-oily lubricity and "after feel", in combination with favorable emolliency, skin compatability and moisturization characteristics. The present compounds exhibit a parity with the cyclomethicones with respect to those features which are desireable, and an advantage compared to the cyclomethicones with respect to those features which are less desirable. Quite unexpectedly, the emollient compound(s) of the present invention may be used generally as substitutes exhibiting the same or more favorable characteristics for the cyclomethicones in dermatological products.

The present invention contemplates lotion and cream bases, oil-in-water and water-in-oil emulsion compositions, stick bases and dispersible and Non-dispersible (floating) bath oil bases and compositions. In base compositions according to the present invention, capryl isostearate is formulated with a stiffening or hardening agent (stick base), an emulsifier (lotion base), a dispersing agent (dispersible oil base) or a second emollient such as mineral oil or a vegetable oil. Stick bases pursuant to the present invention comprise about 40–75% capryl isostearate in combination with about 25–60% of a stiffening agent. The stiffening agent is most preferably di-behenyl fumarate and is included in an amount preferably ranging from about 30% to about 50% by weight of the stick base composition. Stick bases according to the present invention may be further formulated as deodorant compositions, wherein capryl isostearate and the stiffening or hardening agent is combined with an effective amount of at least one additional additive selected from the group consisting of thickening agents, deodorant compounds, fragrances, emulsifiers, skin and hair conditioning agents, coloring agents/pigments, humectants, preservatives, anti-oxidants and oil soluble "actives" and medicaments, among others. In instances where the stick base and additional additives are included in a composition, the stick base preferably comprises about 35% to about 99% by weight of the composition, more preferably about 50% to about 95% by weight of the composition, the remainder of the composition being made up by one or more of additive selected from the group consisting of thickening agents, deodorant compounds, fragrances, emulsifiers, skin and hair conditioning agents, coloring agents/pigments, humectants, preservatives, anti-oxidants and oil soluble "actives" and medicaments, among others.

An oil-in-water emulsion base composition (oil phase) according to the present invention comprises about 50% to about 99% of capryl isostearate and about 1% to about 50% of an emulsifier, more preferably about 75% to about 99% by weight of capryl isostearate and about 1% to about 25% by weight of an emulsifier, even more preferably about 85% to about 99% by weight of capryl isostearate and about 1% to about 15% by weight of an emulsifier. The oil-in-water emulsion base (oil phase) may be added to a mixture of water and a thickener in an amount effective for thickening the final lotion composition which contains the oil phase, water and a thickener. Thickening agents, such as magnesium aluminum silicate, xanthan gum, alkoxylated cellulose thickeners, carboxylmethyl cellulose and hydroxypropyl cellulose among other cellulose thickeners and karaya gum, among numerous others, may be included in amounts ranging from about 0.01% to about 5% by weight or more of the final oil-in-water emulsion composition (which includes oil phase, water and thickener). The thickening agent is generally added to a water phase before combining with the oil phase to produce oil-in-water lotion and cream compositions. In addition to capryl isostearate and emulsifier, oil-in-water emulsion compositions include amounts of water ranging from about 45% to about 95%, more preferably about 60% to about 80% by weight of the final composition. When water and thickener are added to the oil-in-water emulsion base composition, the resulting composition is an oil-in-water emulsion composition, which may be a lotion or a cream.

A water-in-oil emulsion base (oil phase) composition according to the present invention comprises about 50% to about 99% by weight of capryl isostearate, about 0.5% to about 25% by weight of a stiffening or hardening agent (as previously described) and about 0.5% to about 25% by weight of an emulsifier as previously described. In preferred aspects of this invention, the capryl isostearate comprises about 50% to about 96% by weight of the base composition, the thickener comprises about 2% to about 15% by weight of the base composition and the emulsifier comprises about 2% to about 15% by weight of the base composition. The water-in-oil emulsion base composition described above may be used to produce a water-in-oil emulsion compositions comprising about 15% to about 75% by weight water and about 25% to about 85% by weight of the water-in-oil emulsion base composition described above, more preferably about 60–70% water and about 30–40% of the emulsion base composition, even more preferably about two thirds (66.67%) by weight water and about one third (33.33%) by weight of the water-in-oil emulsion base composition. Hardening or stiffening agents for use in this aspect of the present invention include, for example, di-behenyl fumarate (Marrix® 222, available from Bernel Chemical Co., Englewood, N.J.), carnauba wax, beeswax, paraffin wax, ozokerite wax, fatty alcohols such as stearoyl alcohol and stearic monoethanolamide, among others. Di-behenyl furmarate is preferred. It is noted here that although the term hardening or stiffening agent is used here to describe these additives, the term oil phase thickening agent also may be used to describe the hardening or stiffening agents used here. They have a similar effect as the thickening agents in the oil-in-water emulsion compositions, but are chemically distinguishable.

Oil-in-water emulsion compositions and water-in-oil emulsion compositions may also optionally contain at least one additive selected from the group consisting of fragrances, skin and hair conditioning agents, coloring agents/pigments, humectants, preservatives, anti-oxidants and oil soluble "actives" and medicaments, among others.

In another aspect of the present invention, a dispersible bath oil is contemplated, the bath oil comprising about 75% to about 97.5% by weight of capryl isostearate and about 2.5% to about 25% by weight of a dispersing agent. Another aspect of the present invention relates to a floating (Non-dispersible) bath oil which comprises about 1% to about 99% by weight of capryl isostearate and about 1% to about 99% by weight of an oil emollient (other than capryl isostearat), preferably mineral oil (for example, Kaydol or Blandol from Witco Chemical Co.) or a vegetable oil, such as canola oil. Alternatively, effective amounts of a spreading agent such as sodium dioctyl sulfosuccinate may be included with the capryl isostearate (the oil emollient may be excluded, if desired) in the floating bath oil composition in order to spread the capryl isostearate on the surface of the water upon use. Preferred floating bath oil compositions may preferably comprise about 10% to about 90% by weight of capryl isostearate and about 10% to about 90% of an oil emollient, with more emollient oil being included in the Non-dispersible (floating) bath oil composition as a function of the cost compared to capryl isostearate. More preferably, floating bath oils comprise about 0.5% to about 10% by weight of a spreading agent, with the remainder of the composition comprising capryl isostearate or a mixture of capryl isostearate and an emollient oil other than capryl isostearate. Even more preferably, capryl isostearate, mineral oil and vegetable oil (preferably, canola oil) are included in the Non-dispersible (floating) bath oil compositions in a ratio of about 1:1:1, the remainder of the composition preferably comprising spreading agent. The amount of capryl isostearate may vary over a wide weight range because capryl isostearate is soluble in vegetable oil, mineral oil and other traditional emollient oils in all proportions, which provides tremendous flexibility in formulation.

The present compounds are preferably "all green", i.e. they are produced utilizing components which are derived from plants (castor oil and tall oil). Alternatively, the components which are utilized to make capryl isostearate may be prepared synthetically by methods which are well known in the art. Capryl alcohol is preferably obtained from the oxidative cleavage of castor oil followed by the reduction of methyl hexyl ketone to capryl alcohol (2-octanol) by methods which are well known in the the art. Isostearic acid is obtained from the dimerization and hydrogenation of tall oil (available from Union Camp Corp., Jacksonville, Fla.).

Emollient compounds according to the present invention are synthesized by well known procedures in the art, generally, by reacting capryl alcohol and isostearic acid at elevated temperatures followed by standard isolation procedures.

A method of instilling emolliency to dermatological compositions according to the present invention is also contemplated, the method comprising adding an effective amount of capryl isostearate to a dermatological formulation. The dermatological formulations which result exhibit a dry, non-oily lubricity, lasting emolliency and moisturizing characteristics.

In another method of the present invention, capryl isostearate may be used as a substitute for cyclomethicones in dermatological formulations, the resulting compositions containing capryl isosterate exhibiting parity with respect to the initial non-oily lubricity and emolliency of cyclomethicone-containing compositions, but with lasting emolliency and moisturizing characteristics. These characteristics represent an unexpected result.

Having generally described the invention, reference is now made to the following examples which are intended to illustrate preferred embodiments and comparisons. The included examples are not to be construed as limiting the scope of this invention as is more broadly set forth above and in the appended claims.

EXAMPLES

Example 1

Synthesis of Capryl Isostearate 1 mole of capryl alcohol is reacted with 1 mole isostearic acid using standard ester manufacturing procedures (heated at elevated temperatures, preferably about 160–180° C. with 0.1% by weight of the reactants of a catalyst such as tin oxalate or dibutyl tin oxide) either neat or in inert solvent in standard manufacturing equipment until the production of water from the esterification is complete and an appropriate SAP value and acid value are reached. The compound is isolated by distilling off excess solvent, if present and then either distilling off the emollient compound, extracting out the capryl isostearate, or precipitating the emollient compound out of water.

Example 2

Lotion Composition

| Compound | Parts By Weight |
| --- | --- |
| Phase A | |
| Emulsifier (Propylene glycol-isoceteth-3-acetate) Hetester ® PHA | 10.0 |
| Capryl isostearate | 15.0 |
| Phase B | |
| Water (deionized) | 73.7 |
| Veegum | 0.8 |
| Keltrol | 0.4 |
| Preservative | 0.1 |

Procedure: Mix phase A at room temperature. Mix phase B at room temperature until completely dispersed. With proper mixing, add phase A to phase B at room temperature to provide an oil-in-water lotion composition.

Comments:

1. Compound of the present invention is an excellent emollient for use in creams and lotions and provides plasticization as well as a moisturizing, but dry non-oily skin effect.

2. Optional pulverized pigment formulation as described below may be added to lotion from about 0.5 to 15 parts pigment composition to about 85–99.5 parts of the above-described lotion, more preferably about 0.5 to about 10 parts.

| Pigment Formulation (Added in order written, then pulverized and mixed to uniformity) | |
| --- | --- |
| Component | Weight Percent |
| $TiO_2$ | 70.0% |
| Yellow Iron Oxide | 12.0% |
| Red Iron Oxide | 5.0% |
| Black Iron Oxide | 2.0% |
| Talc | 11.0 |
| | 100 percent total |

Comments:

1. Pigments readily available from commercial sources such as Wittaker, Clark & Daniels. Black iron oxide available from Sun Chemical Co.

2. Composition is obtained by mixing components and then pulverizing or micronizing mixture before combining with other components to produce compositions according to the present invention.

3. Pigmented lotions, creams, sticks, etc. can be used as skin staining products or sunburn protective products (sunblockers).

Example 3

Stick Base

| Compound | Parts By Weight |
| --- | --- |
| Capryl isostearate | 50.0 |
| Dibehenyl fumarate (Marrix ® 222, Bernel) | 50.0 |
| | 100.0 Parts Total |

Comments:

1. Components are mixed, then heated to 80° C., then cooled to produce a homogeneous stick base, which provides unique characteristics including a dry, non-oily feel along with surprisingly good moisturization.

2. Stick base may be used to produce deodorants, lipsticks, other cosmetic compositions.

3. Pigments may be added to the stick base in amounts ranging from about 0.5 to about 15% to produce lipsticks, other body staining compositions.

Example 4

Dispersible Bath Oil

| Compound | Parts By Weight |
| --- | --- |
| Capryl isostearate | 80–90 |
| Propyleneglycol-isoceteth-3-acetate | 10–20 |
| (Hetester ® PHA, Bernel) | 100 Parts Total |

Comments:

1. Components are mixed at room temperature to produce dispersible bath oil, which provides unique dry, non-oily feel with lasting emolliency and moisturizing characteristics.

Example 5

Water-in-Oil Cream Composition

The following components were combined in two separate phases, phase A, the oil phase and phase B, the water phase. After complete mixing of phases A and B, phase C was added at elevated temperature and mixed with the other components to produce a flowing lotion.

| | | Weight % |
| --- | --- | --- |
| Phase A: | "BSA" (1) | 2.30 |
| (heat to 85° C. and mix) | DiBehenyl Fumarate | 8.00 |
| | White Petrolatum | 10.00 |
| | Mineral Oil (Kaydol) | 28.45 |
| | Capryl isostearate | 15.00 |
| | DEA Cetyl Phosphate (amphisol) (3) | 0.50 |
| | Propyl Paraben | 0.10 |
| Phase B: | | |
| (heat to 85° C.) | Water, deionized | 33.30 |
| | Borax, N.F. | 1.10 |

-continued

|  | Weight % |
|---|---|
| Phase C: | |
| (add to emulsion Fumed SiO₂ (cabosil) at 75–80° C.) | 1.25 |
| 100.0% total | |

(1) 12-Behenoyl hydroxystearic acid (BSA)- prepared by reacting 1 mole of Behenic acid, 1 mole of 1 2-hydroxy stearic acid and 0.1% by weight dibutyl tin oxide (based upon the total weight of the reactants). These individual components were charged to a glass vessel equipped with proper mixer and a water trap to collect water. The components were mixed and heated at 200° C. until the desired saponification value, hydroxyl value and acid value are achieved. "Typical" Assay for BSA (not a specification)

| sap value | = | 161.5 |
|---|---|---|
| acid value | = | 104.5 |
| hydroxyl value | = | 7.5 |
| color (melted) | = | gardner 2+ |
| melting point | = | 68° C. |

(3) Amphisol available from Hoffmann-LaRoche, Nutley, N.J.

Procedure:

Add B to A at 85° C. Mix without aeration. Cool and add C at 75–80° C.; continue to mix until homogeneous and cool to approximately 55° C. Package at 55° C.

Note: the "BSA" 1 is the primary emulsifier, however, this emulsion uses 2 auxilliary emulsifiers with "BSA". They are amphisol and cabosil. The di-behenyl fumarate functions to thicken or harden this composition.

Unusual emolliency of capryl isostearate provides a light feel that improves the greasiness/oiliness of the petrolatum and makes for a drier composition (plasticizes greasiness/oiliness) containing petrolatum and water which is more cosmetically elegant (non-greasy).

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. A base composition for use in formulating an oil-in-water dermatological composition consisting essentially of:
   i) about 50% to about 99% by weight of an emollient compound of the chemical formula:

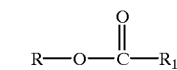

where R is CH₃(CH₂)₅CH— and

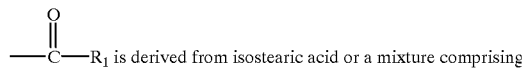

where R is $CH_3(CH_2)_5CH-$ and $-C-R_1$ is derived from isostearic acid or a mixture comprising isostearic acid and stearic acid wherein the weight ratio of isostearic acid to stearic acid in said mixture ranges from approximately 20:1 to 1:1 and
   ii) about 1% to about 50% by weight of an emulsifier, said emollient compound being included in said base composition in an amount effective to instill the characteristics of non-oily lubricity, after feel, lasting emolliency and moisturization in said oil-in-water dermatological composition.

2. The base composition according to claim 1 wherein said emollient compound comprises about 75% to about 99% by weight of said composition and said emulsifier comprises about 1% to about 25% by weight of said composition.

3. The base composition according to claim 1 wherein said emulsifier is selected from the group consisting of propylene glycol-isoceteth-3-acetate, glycerylmonostearate cetearyl alcohol, ceteareth-20 and mixtures, thereof.

4. The base composition according to claim 1 wherein said emollient compound comprises about 85% to about 99% by weight of said composition and said emulsifier comprises about 1% to about 15% by weight of said composition.

5. An oil-in-water emulsion composition comprising:
   a). a base composition consisting essentially of:
      i) about 50% to about 99% by weight of an emollient compound of the chemical formula:

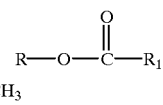

where R is CH₃(CH₂)₅CH— and

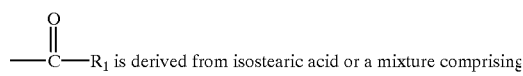

where R— is $CH_3(CH_2)_5CH-$ and $-C-R_1$ is derived from isostearic acid or a mixture comprising, isostearic acid and stearic acid wherein the ratio of isostearic acid to stearic acid in said mixture ranges from approximately 20:1 to 1:1 and
      ii) about 1% to about 50% by weight of an emulsifier; and
   b) a water and thickener mixture comprising:
      i) about 94% to about 99.985% by weight water and about 0.015% to about 6% by weight of a thickener; said water and thickener mixture comprising about 25% to about 90% by weight of said emulsion composition, said thickener comprising about 0.01% to about 5% by weight of said emulsion composition, said emollient compound instilling the characteristics of non-oily lubricity, after feel, lasting emolliency and moisturization in said oil-in-water composition.

6. The composition according to claim 5 further comprising an effective amount of an additive selected from the group consisting of deodorant compounds, fragrances, skin and hair conditioning agents, coloring agents/pigments, humectants, preservatives, anti-oxidants, oil soluble medicaments and mixtures, thereof.

7. The composition according to claim 5 wherein said emulsifier is selected from the group consisting of propylene glycol-isoceteth-3-acetate, glycerylmonostearate cetearyl alcohol, ceteareth-20 and mixtures, thereof.

8. The composition according to claim 5 wherein said thickener is selected from the group consisting of magnesium aluminum silicate, xanthan gum, cellulose thickeners, karaya gum and mixtures, thereof.

9. The composition according to claim 8 wherein said cellulose thickeners are selected from the group consisting of carboxylmethyl cellulose, hydroxypropyl cellulose and hydroxymethyl cellulose.

10. A method of instilling the characteristics of non-oily lubricity, after feel, lasting emolliency and moisturization in a dermatological composition comprising the step of adding to said dermatological composition an effective amount of capryl isostearate as an emollient compound.

* * * * *